United States Patent [19]
Shen et al.

[11] Patent Number: 5,430,815
[45] Date of Patent: Jul. 4, 1995

[54] OPTICAL FIBER WATER SENSOR

[75] Inventors: Nelson M. Shen; David A. Horsma, both of Palo Alto, Calif.; Marc F. Moisson, Leuven, Belgium; Narendra Kulkarni, Sunnyvale, Calif.

[73] Assignee: Raychem Corporation, Menlo Park, Calif.

[21] Appl. No.: 14,040

[22] Filed: Feb. 5, 1993

[51] Int. Cl.⁶ .......................... G02B 6/00; H01J 5/16; G01N 5/02
[52] U.S. Cl. ........................ 385/13; 385/12; 385/140; 385/147; 250/227.11; 250/227.14; 250/227.16; 250/227.25; 73/73; 73/800
[58] Field of Search ............ 385/12, 13, 140, 27, 385/29, 32, 48, 100, 147; 250/227.11, 227.14, 227.16, 227.25, 573; 73/73, 800

[56] References Cited

U.S. PATENT DOCUMENTS

| | | | |
|---|---|---|---|
| 4,159,420 | 6/1979 | Tsunoda | 250/227.25 X |
| 4,221,962 | 9/1980 | Black et al. | 250/227.25 X |
| 4,443,700 | 4/1984 | Macedo et al. | 250/227.16 X |
| 4,634,856 | 1/1987 | Kirkham | 250/227.25 X |
| 4,637,729 | 1/1987 | Schoch | 250/227.25 X |
| 4,729,630 | 3/1988 | Martinez | 385/13 |
| 4,750,796 | 7/1988 | Shibata et al. | 385/13 |
| 4,812,014 | 3/1989 | Sawano et al. | 385/13 |
| 4,891,511 | 1/1990 | Reed | 250/227.16 |
| 4,918,305 | 4/1990 | Wlodarczyk et al. | 250/227.14 |
| 4,926,165 | 5/1990 | Lahlouh et al. | 340/603 |
| 5,082,719 | 1/1992 | Arroyo | 428/219 |
| 5,138,152 | 8/1992 | Botting | 250/227.16 |
| 5,157,752 | 10/1992 | Greveling et al. | 385/112 |
| 5,193,129 | 3/1993 | Kramer | 385/13 |
| 5,222,165 | 6/1993 | Bohlinger | 385/16 |
| 5,243,670 | 9/1993 | Bonicel | 385/13 |
| 5,262,640 | 11/1993 | Purvis et al. | 250/227.25 |

FOREIGN PATENT DOCUMENTS 2100420 12/1982 United Kingdom ............ 385/12 X

OTHER PUBLICATIONS

Sawano et al., "Optical Fiber Cable with Submersion Sensor Fiber", IW & C Symposium Proceedings, 1987, p. 284.
"Proceedings of 36th Intl Wire & Cable Symposium" Dec. 1, 1987.
Patent Abstracts of Japan vol. 13, No. 30 (P-816) 24 Jan. 1989 (Hiroyuki) abst. only.
Patent Abstracts of Japan vol. 13, No. 82 (P-833) 23 Feb. 1989 (Masayuki) abst. only.
Patent Abstracts of Japan vol. 11, No. 164 (P-580) 27 May 1987 (Kuwaki) abst. only.
Journal of Lightwave Technology, vol. 8, No. 12, Dec. 1, 1990 pp. 1820–1832.

*Primary Examiner*—Brian Healy
*Attorney, Agent, or Firm*—Herbert G. Burkard; A. Stephen Zavell

[57] ABSTRACT

An optical fiber water sensor includes a mandrel having a convex or concave shape adjacent to an optical fiber which is adjacent to a water swellable material held in a reservoir. Upon coming in contact with water, the material swells and deforms a section of the optical fiber about a contour defined by the mandrel thus attenuating a signal propagating through the fiber which is detected by an optical detector to indicate the presence of water.

17 Claims, 1 Drawing Sheet

OPTICAL FIBER WATER SENSOR

BACKGROUND OF THE INVENTION

The present invention relates to optical fiber sensors for detecting liquids.

Various optical fiber water sensors have been proposed in the prior art. Sawano et al. "Optical fiber cable with submersion sensor fiber", International Wire & Cable Symposium Proceedings 1987, p. 284, discloses an optical fiber water sensor whereby a water swellable material is disposed in a cavity adjacent a piston which confronts an optical fiber which in turn confronts a concave mandrel. Upon being exposed to water, the water swellable material swells, which urges the piston against the fiber and causes the fiber to assume a shape of the concave mandrel. This sensor is disadvantages since it is relatively complicated in design and hence expensive.

Sawano et al. further describe an optical fiber sensor whereby an optical fiber is helically wrapped about a rod composed of a water swellable material, with a stiff yarn being counter-helically wound around the rod. Upon coming in contact with water, the water swellable material swells and causes the optical fiber to bend at a plurality of points about the stiff counter-helically wound yarn. A yarn sensor merely produces a loss over a length of the yarn, rather than at a discrete point. Hence a loss trace of an OTDR looks like a high attenuation fiber instead of a step loss such as a splice and produces poor resolution. In addition, this sensor again is relatively complicated in design, takes up a relatively large amount of space, and hence is inconvenient to deploy.

SUMMARY OF THE INVENTION

Accordingly, it is an object of the present invention to eliminate the above-noted drawbacks of prior art sensors and to provide an optical fiber water sensor which is relatively simple in design, inexpensive to produce, and is relatively compact in size so as to allow the sensor to be deployed in environments where space is at a premium, such as optical fiber closures in telecommunication outside plant environments.

These and other objects of the invention are achieved by an optical fiber water sensor, comprising:
- a substrate having a curved mandrel formed on a side thereof;
- an optical fiber disposed adjacent the mandrel and being oriented such that it can be deflected around a curved contour of the mandrel upon being urged toward the mandrel;
- a liquid swellable material disposed adjacent the optical fiber and oriented such that upon coming in contact with a liquid the material swells and urges the optical fiber around the curved contour, the curved contour having a radius of curvature smaller than a minimum bend radius of the fiber.

BRIEF DESCRIPTION OF THE DRAWING(S)

DESCRIPTION OF THE PREFERRED EMBODIMENTS

Figure 1:
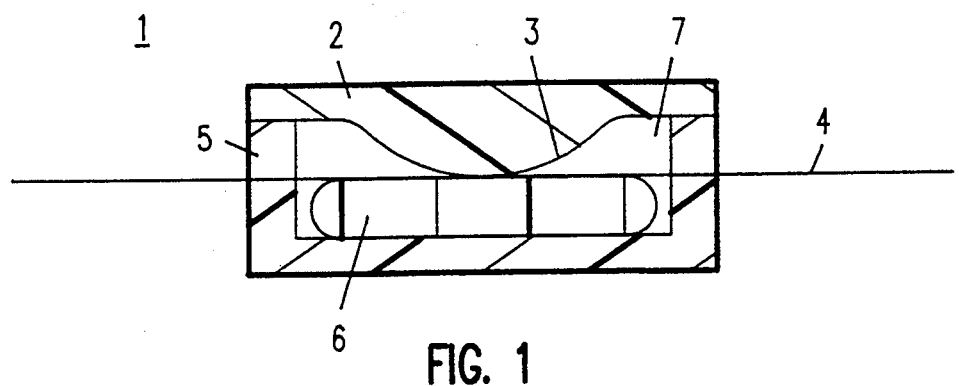
FIG 1 illustrates a first preferred embodiment of an optical fiber water sensor according to the present invention.

FIG 1 illustrates a first preferred embodiment of the invention. Referring to this figure, an optical fiber water sensor I comprises a substrate 2 having a convex shaped mandrel 3 on one end thereof. The convex mandrel has a minimum radius of curvature which is less than a minimum bend radius for optical fiber 4 such that upon bending a portion of the optical fiber 4 about the convex mandrel 3 attenuation to a signal propagating in the optical fiber 4 results. The attenuation is detectable by any convenient means, such as a photodetector or optical time domain reflectometer (OTDR). The sensor 1 further includes a second substrate 5 having a reservoir 7 therein which contains a material 6 which swells when exposed to a liquid. The liquid or water swellable material can comprise a gel, rubber, or polymer, as desired. Examples of swellable materials well known in the art, and are specifically disclosed in Lahlouh et al. U.S. Pat. No. 4,926,165; Greveling et al. U.S. Pat. No. 5,157,752; and Arroyo U.S. Pat. No. 5,082,719, the disclosures of which are all incorporated herein by reference. Preferably, the water swellable material should be made of a material which is induction free, provides sufficient expandability to allow measurement by an OTDR when several sensors are cascaded together, is of a type that expands regardless of the kind of water or liquid present, and which operates over a broad temperature range, such as $-40°$ C. to $+60°$ C. A sector angle formed when the water swellable material is fully saturated is preferably greater than 15°, 20°, 25°, 30°, 35°, 40°, 45°, 60°, 90°, 180°, and higher depending on the sector angle chosen and total attenuation desired. The substrates 2, 5 can be made of any desired material, such as plastic, and can be secured together by screws, clamps, adhesive, etc. The minimum bend radius defined by the convex mandrel should be less than the minimum bend radius of the fiber. For single mode glass-on-glass fiber, a minimum bend radius of the mandrel optionally should be less than 15 mm, 12 mm, 10 mm, 9 mm, 7 mm, 6 mm, 5 mm, or 4 mm.

Figure 2:
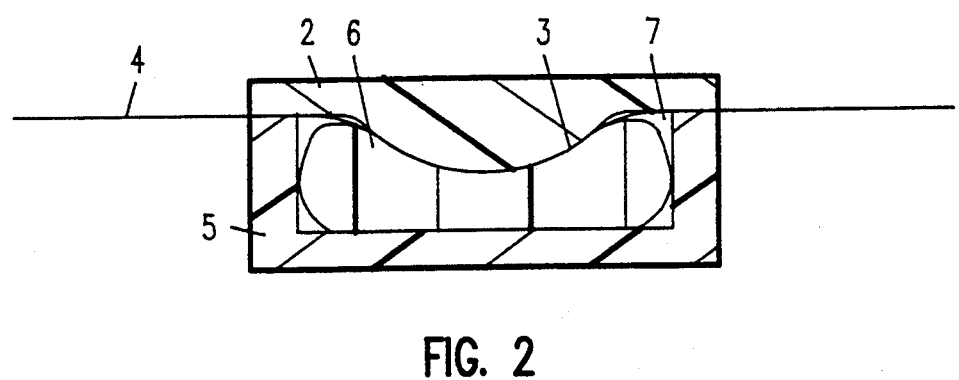
FIG. 2 illustrates the sensor of FIG I after exposure to water.

Upon exposing the water swellable material to water, it swells and urges the fiber 4 to assume a shape of the convex mandrel 3, as illustrated in FIG. 2. Since the fiber 4 is bent about a radius of curvature smaller than its minimum bend radius, an attenuation to a signal propagating in the optical fiber results which is readily detectable by any detection means.

Figure 3:
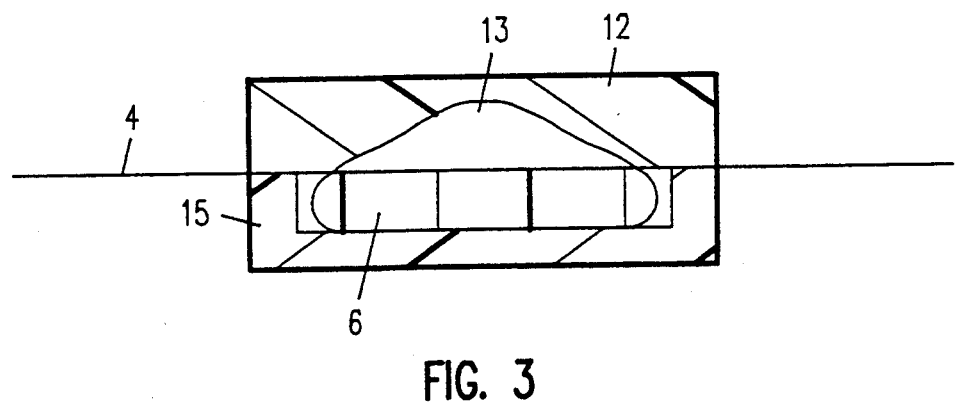
FIG. 3 illustrates an alternative preferred embodiment of the invention.

FIG. 3 illustrates an alternative embodiment of the invention whereby the substrate 2 is replaced by substrate 12 having a concave shaped mandrel 13 on one side thereof, with another substrate 15 containing the water swellable material 6. Upon the water swellable material 6 coming in contact with water and expanding, the optical fiber 4 is bent about a shape defined by the concave mandrel 13. The embodiment of FIG. 3 works well but has a slightly slower response time than the FIG 1 embodiment since at the beginning of swelling the fiber bends about a relatively large bend radius as compared to that initially encountered in FIGS. 1, 2.

A preferred use for the sensor embodiments described are for inclusion in an outside plant optical fiber closure or optical fiber optical network unit.

Table 1 contains test results measured for three sensors constructed according to the present invention and cascaded on an optical fiber, with sensor 3 being closest to an OTDR and sensor 1 being furthermost from the OTDR. All three sensors utilized a convex mandrel having a minimum bend radius of 0.25 inches (6.35 mm) shaped to induce a bend about a sector angle of about 45° for a single mode glass-on-glass fiber. The water swellable material used in each sensor was Aquaquell Seal Tape 7V obtainable from Sumitoma Corporation, the material being a blend of styrene butadiene rubber, sodium acrylate-vinyl alcohol, and chloroprene rubber.

TABLE 1

| Time after immersed in water | Sensor 1 insertion loss (dB) | Sensor 2 insertion loss (dB) | Sensor 3 insertion loss (dB) |
|---|---|---|---|
| Start | 0 | 0 | 0 |
| 15 minutes | 0 | 0 | .28 |
| 50 minutes | .4 | .24 | .35 |
| 1 hour 25 minutes | .4 | .38 | .44 |
| 2 hours | .43 | .46 | .55 |
| 2 hours 50 minutes | .49 | .48 | .65 |
| 18 hours | .86 | 1.12 | .84 |
| 24 hours | .93 | 1.11 | .91 |
| 92 hours | 1.07 | 1.26 | 1.1 |
| 116 hours | .928 | 1.14 | 1.07 |
| 124 hours | 1.3 | 1.16 | 1.05 |
| 141 hours | 1.28 | 1.12 | 1.04 |

As can be seen from the table, the sensors constructed and tested take less than one hour to develop detectable signals and take about a full day to be fully saturated. Preferably, the loss induced by each sensor is designed to be about 1 dB when the sensor is fully saturated. A reason to limit the loss to 1 dB is to allow a cascade arrangement of multiple sensors to be monitored simultaneously. Accordingly, according to a preferred feature of the invention, the sensors are constructed so as to create a total loss in a fiber which does not exceed 1.5 dB, 1.25 dB, 1.15 dB, and optimally 1.0 dB.

Though the invention has been described by reference to certain preferred embodiments, the invention is not to be limited thereby and only by the appended claims.

What is claimed is:

1. An optical fiber water sensor, comprising:
   a substrate having a curved mandrel formed on a side thereof;
   an optical fiber disposed adjacent the mandrel and being oriented such that it can be deflected around a curved contour of the mandrel upon being urged toward the mandrel;
   a liquid swellable material disposed adjacent the optical fiber and oriented such that upon coming in contact with a liquid the material swells and urges the optical fiber around the curved contour, the curved contour having a radius of curvature smaller than a minimum bend radius of the fiber, wherein the minimum bend radius is less than 7 millimeters, the fiber being bent about a sector angle greater than 30°, and the liquid swellable material when saturated introduces a loss in the optical fiber which is less than 1.25 db.

2. The sensor of claim 1, further comprising a second substrate having a reservoir therein which contains the liquid swellable material.

3. The sensor of claim 1, the curved mandrel having a convex shape.

4. The sensor of claim 1, the curved mandrel having a concave shape.

5. The sensor of claim 1, the swellable material comprising a rubber or a gel which swells upon exposure to water.

6. An optical fiber water sensor, consisting essentially of: a substrate having a curved mandrel formed on a side thereof;
   an optical fiber disposed adjacent the mandrel and being oriented such that it can be deflected around a curved contour of the mandrel upon being urged toward the mandrel;
   a liquid swellable material disposed adjacent the optical fiber and oriented such that upon coming in contact with a liquid the material swells and urges the optical fiber around the curved contour, the curved contour having a radius of curvature smaller than a minimum bend radius of the fiber, wherein the minimum bend radius is less than 7 millimeters, the fiber being bent about a sector angle greater than 30°, and the liquid swellable material when saturated introduces a loss in the optical fiber which is less than 1.25 db.

7. The sensor of claim 6, further comprising a second substrate having a reservoir therein which contains the liquid swellable material.

8. The sensor of claim 6, the curved mandrel having a convex shape.

9. The sensor of claim 8 wherein the optical fiber is adjacent the curved convex shaped mandrel and the liquid swellable material.

10. The sensor of claim 6, the curved mandrel having a concave shape.

11. The sensor of claim 6, the swellable material comprising a rubber or a gel which swells upon exposure to water.

12. An optical fiber water sensor, comprising:
    a substrate having a curved mandrel formed on a side thereof;
    an optical fiber disposed adjacent the mandrel and being oriented such that it can be deflected around a curved contour of the mandrel upon being urged toward the mandrel;
    a liquid swellable material disposed adjacent and along a length of the optical fiber and oriented such that upon coming in contact with a liquid the material swells and urges the optical fiber around the curved contour, the curved contour having a radius of curvature smaller than a minimum bend radius of the fiber, wherein the minimum bend radius is less than 7 millimeters, the fiber being bent about a sector angle greater than 30°, and the liquid swellable material when saturated introduces a loss in the optical fiber which is less than 1.25 db.

13. The sensor of claim 12, further comprising a second substrate having a reservoir therein which contains the liquid swellable material.

14. The sensor of claim 12, the curved mandrel having a convex shape.

15. The sensor of claim 14 wherein the optical fiber is adjacent the curved convex shaped mandrel and the liquid swellable material.

16. The sensor of claim 12, the curved mandrel having a concave shape.

17. The sensor of claim 3 wherein the optical fiber is adjacent the curved convex shaped mandrel and the liquid swellable material.

* * * * *